(12) United States Patent
Weiburg et al.

(10) Patent No.: US 9,044,383 B1
(45) Date of Patent: Jun. 2, 2015

(54) COMPOUNDS AND METHODS FOR DRUG DELIVERY VIA A HUMAN NAIL

(71) Applicants: Anthony Weiburg, Staten Island, NY (US); Janet Weiburg, Staten Island, NY (US)

(72) Inventors: Anthony Weiburg, Staten Island, NY (US); Janet Weiburg, Staten Island, NY (US)

( * ) Notice: Subject to any disclaimer, the term of this patent is extended or adjusted under 35 U.S.C. 154(b) by 103 days.

(21) Appl. No.: 14/063,027

(22) Filed: Oct. 25, 2013

(51) Int. Cl.
| | |
|---|---|
| *A01N 43/16* | (2006.01) |
| *A61K 31/35* | (2006.01) |
| *A01N 25/00* | (2006.01) |
| *A61K 47/00* | (2006.01) |
| *A61K 9/00* | (2006.01) |
| *A61K 31/352* | (2006.01) |

(52) U.S. Cl.
CPC .............. *A61K 9/0012* (2013.01); *A61K 31/352* (2013.01)

(58) Field of Classification Search
CPC .......................... A61K 9/0012; A61K 31/352
See application file for complete search history.

(56) References Cited

U.S. PATENT DOCUMENTS

| | | | |
|---|---|---|---|
| 5,017,368 A | 5/1991 | Sugiyama et al. | |
| 5,807,540 A | 9/1998 | Junino et al. | |
| 7,025,953 B2 | 4/2006 | Blin et al. | |
| 7,572,933 B2 | 8/2009 | Gupta | |
| 2003/0082129 A1 | 5/2003 | Buckingham et al. | |
| 2009/0169652 A1 | 7/2009 | Osborne | |
| 2012/0128777 A1 | 5/2012 | Keck et al. | |
| 2013/0146077 A1 | 6/2013 | Cooke et al. | |

OTHER PUBLICATIONS

Godard, et al., Body Composition and Hormonal Adaptations Associated with Forskolin, abstract only 2005.
Greenway, F.L. et al., Topical fat reduction. Obesity Res, 1995.
K. A. Walters and G. L. Flynn, Permeability characteristics of the human nail plate, International Journal of Cosmetic Science 5, 231-246 (1983).
Onakpoya, et al., The Use of Garcinia Extract (Hydroxycitric Acid) (2011).
Sigma-Aldrich, Inc., Forskolin, Sigma.com, 2014.
Hussain, T., Vegan Nail Polish—Why?, Feb. 6, 2013, www.epsfootdocs.com.
Majeed, M. and Lakshmi, P., Coleus Forshohlii Extract (95% forskolin), 2013.
Mishra, R.K., Ayurvedic Marma Therapy for Today's Health Needs, Oct. 1, 2013, healing.about.com/cs/uc_directory/a/uc_marmatherapy.htm.

*Primary Examiner* — Gina Justice
*Assistant Examiner* — Genevieve S Alley
(74) *Attorney, Agent, or Firm* — Michael J. Feigin, Esq.; Feigin & Associates, LLC

(57) ABSTRACT

Embodiments of the disclosed technology are directed to methods and/or compositions for preparing a nail coating composition with forskolin to be delivered into the human body. The composition is formed of forskolin and nitrocellulose dissolved in a solvent. The solvent may be an organic solvent and may further comprise a resin, an adhesive polymer, a plasticizer, a coloring agent, and/or any other constituent known to be used in nail coating compositions. The composition is applied to the fingertips and/or fingernails of an individual such that the forskolin contained in the composition is absorbed via the nail plate into the body. The surface of the nail plate may be primed or otherwise manipulated to promote a higher absorption rate.

19 Claims, 5 Drawing Sheets

COMPOUNDS AND METHODS FOR DRUG DELIVERY VIA A HUMAN NAIL

FIELD OF THE DISCLOSED TECHNOLOGY

The disclosed technology relates generally to drug delivery systems, and more particularly to transdermal weight loss drug absorption through mammalian nails and/or claws.

BACKGROUND OF THE DISCLOSED TECHNOLOGY

Many products and compounds exist which claim to effectuate weight loss in humans. Some have better results and reputations than others. In recent years, people have begun to scrutinize what sort of chemicals and compounds they put into their bodies. While synthetic drugs and compounds for weight loss may achieve more desirable outcomes, they also frequently result in negative side effects. Often, the long term side effects of such drugs are unknown, as the drugs have not been in use for an extended period of time.

As such, many researchers and scientists have begun to look to natural drugs and compounds for treatments of common conditions such as obesity. One such naturally occurring compound, which has been tied to weight loss, is found in the Indian Coleus plant ('coleus forskohlii'). The compound, forskolin, is used extensively to raise levels of cyclic AMP (cAMP) in the study and research of cell physiology. Cyclic AMP is an important signal carrier necessary for effectuating proper biological response to hormones. Among its many uses, administration of forskolin has shown positive correlative studies in increasing lean mass, bone mass, and testosterone levels in men. Studies have also shown forskolin to be effective in increasing the skin's resistance to UV rays, enhancing the ability of antibiotics to kill bacteria, and reducing urinary tract infections and other types of inflammation.

More recently, studies have proven forskolin's effectiveness as a weight loss aid (See GODARD, et al., *Body Composition and Hormonal Adaptations Associated with Forskolin Consumption in Overweight and Obese Men*. Univ. of Kansas, Dept. of Health, Sport and Exercise Sciences, Applied Physiology Laboratory, Lawrence, Kans. 66045; Aug. 14, 2005). In the study by Godard, the forskolin was taken orally and produced favorable results. ibid. In another study, forskolin was applied topically on the skin, and produced favorable results in decreasing obesity in subjects. (GREENWAY, F. L. et al. *Topical fat reduction*. Obesity Res. 3 Suppl. 4: 561S-568S, 1995). Although the dermatological effects were not the subject of the study, research has shown that applying forskolin may result in increased health and decreased degradation/aging of the skin and hair.

Another naturally occurring compound which may promote weight loss is 'garcinia gummi-gutta,' which is more commonly referred to as 'garcinia cambogia.' Although research to date has not been totally dispositive, the administration of gacinia cambogia may also promote weight loss. (ONAKPOYA, et al. (2011). "*The Use of Garcinia Extract (Hydroxycitric Acid) as a Weight Loss Supplement: A Systematic Review and Meta-Analysis of Randomised Clinical Trials*." Journal of Obesity 2011).

While the full potential of forskolin and other compounds may not have been realized yet, forskolin certainly has proven to have positive effects on the human body. However, absorption and delivery of forskolin and other compounds into the body may be somewhat restricted by conventional topical and/or oral ingestions methods. Thus, needed in the art are more effective systems and methods for introducing forskolin and similar compounds into the human body via the bloodstream.

SUMMARY OF THE DISCLOSED TECHNOLOGY

Therefore, it is an object of the disclosed technology to non-invasively introduce certain health supplements into the human body for increased absorption and health benefits.

In an embodiment of the disclosed technology, a composition of a nail polish is formed of a solvent having nitrocellulose and forskolin dissolved therein. The solvent may be an organic solvent. The organic solvent used may be selected from the following group: ethyl acetate ($C_2H_8O_2$), butyl acetate ($C_6H_{12}O_2$), dimethyl sulfoxide ($C_6H_6OS$), chloroform ($CHCl_3$), ethanol ($C_2H_6O$), toluene ($C_7H_8$), water ($H_2O$), butyl alcohol ($C_4H_{10}O$), xylene ($C_8H_{10}$), and/or formaldehyde ($CH_2O$). The solvent may further use one or more of the following constituents: a resin, an adhesive polymer, a plasticizer, a coloring agent, and/or urea.

In another embodiment of the disclosed technology, a method is used for preparing a forskolin nail coating. A "nail coating," for purposes of this specification, may be any liquid, gel, or partial liquid which may be brought into contact with human fingernails. A first step of the disclosed method involves dissolving forskolin in a solvent. The solvent may be composed of at least 50% ethanol. The forskolin may be concentrated between 0.1 and 100 mg/ml. The next step of the disclosed method involves dissolving nitrocellulose into the solvent until the solvent is composed of between 5% and 20% of nitrocellulose.

In further embodiments, the solvent may be composed of at least 75% ethanol, and between 10% and 15% nitrocellulose. Still further, a plasticizer, a resin and/or an adhesive polymer may be added to the solvent.

In yet another embodiment of the disclosed technology, a method is used for delivering forskolin into the body. A first step of the method is directed to priming a surface of a nail plate of a fingertip. Priming of the nail plate may involve physically altering the nail plate to improve liquid permeability. Techniques of physical alteration may include electrical or mechanical abrasion, acid etching, abiation by lasers, and/or microporation, A next step of the method is directed to applying a coating to the nail plate. The coating may be at least partially composed of forskolin. The coating may be any viscous substance permitting forskolin to be dissolved therein.

In a further embodiment of the disclosed method, an additional step may be provided of applying low-frequency ultrasound to the fingertip to promote permeation through the nail plate. In another embodiment, a step may be provided of applying an electrical current to the fingertip to promote permeation through the nail plate. In still further embodiments, the concentration of forskolin may be between $10^{-4}$ mol/L and $10^{-6}$ mol/L.

It should be understood that the use of "and/or" is defined inclusively such that the term "a and/or b" should be read to include the sets: "a and b," "a or b," "a," "b." Further details are set forth in the detailed description below.

DETAILED DESCRIPTION OF EMBODIMENTS OF THE DISCLOSED TECHNOLOGY

Embodiments of the disclosed technology are directed to methods and/or compositions for preparing a nail coating composition with forskolin to be delivered into the human body. The composition is formed of forskolin and nitrocellulose dissolved in a solvent. The solvent may be an organic solvent and may further comprise a resin, an adhesive polymer, a plasticizer, a coloring agent, and/or any other constituent known to be used in nail coating compositions. The composition is applied to the fingertips and/or fingernails of an individual such that the forskolin contained in the composition is absorbed via the nail plate into the body. The surface of the nail plate may be primed or otherwise manipulated to promote a higher absorption rate.

Embodiments of the disclosed technology will become clearer in view of the following description of the Figures.

Figure 1:
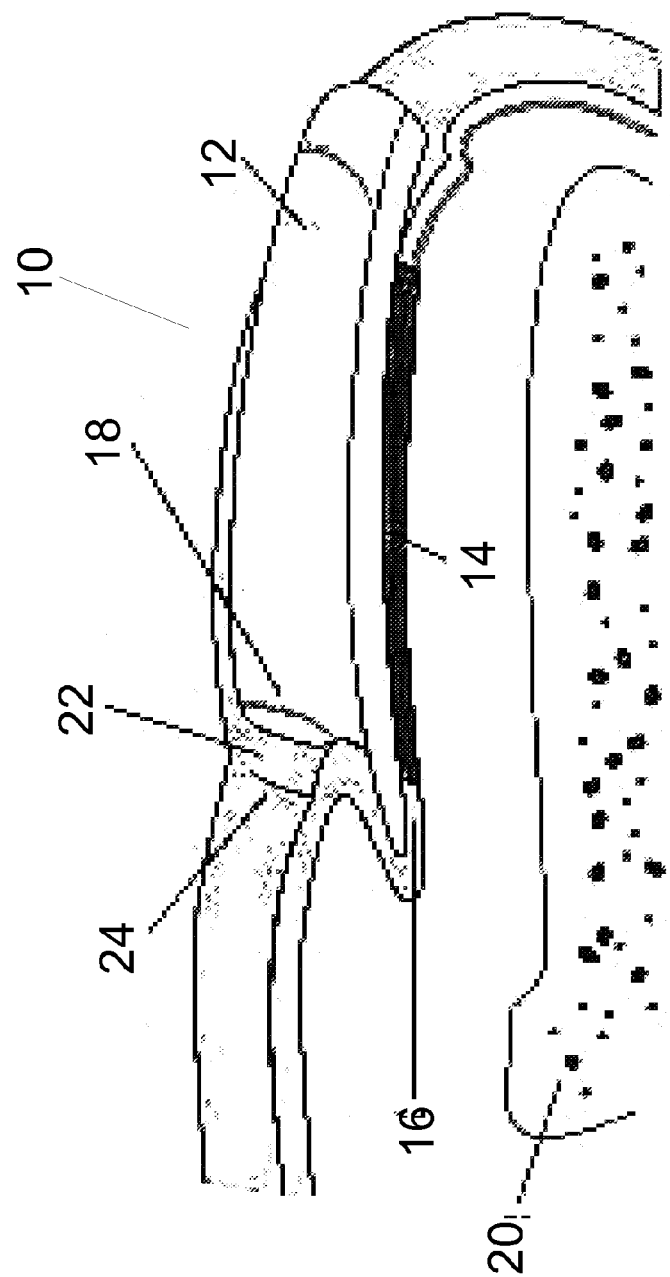
FIG. 1 shows a diagram of nail anatomy onto which an embodiment of the disclosed technology may be used.
Figure 2:
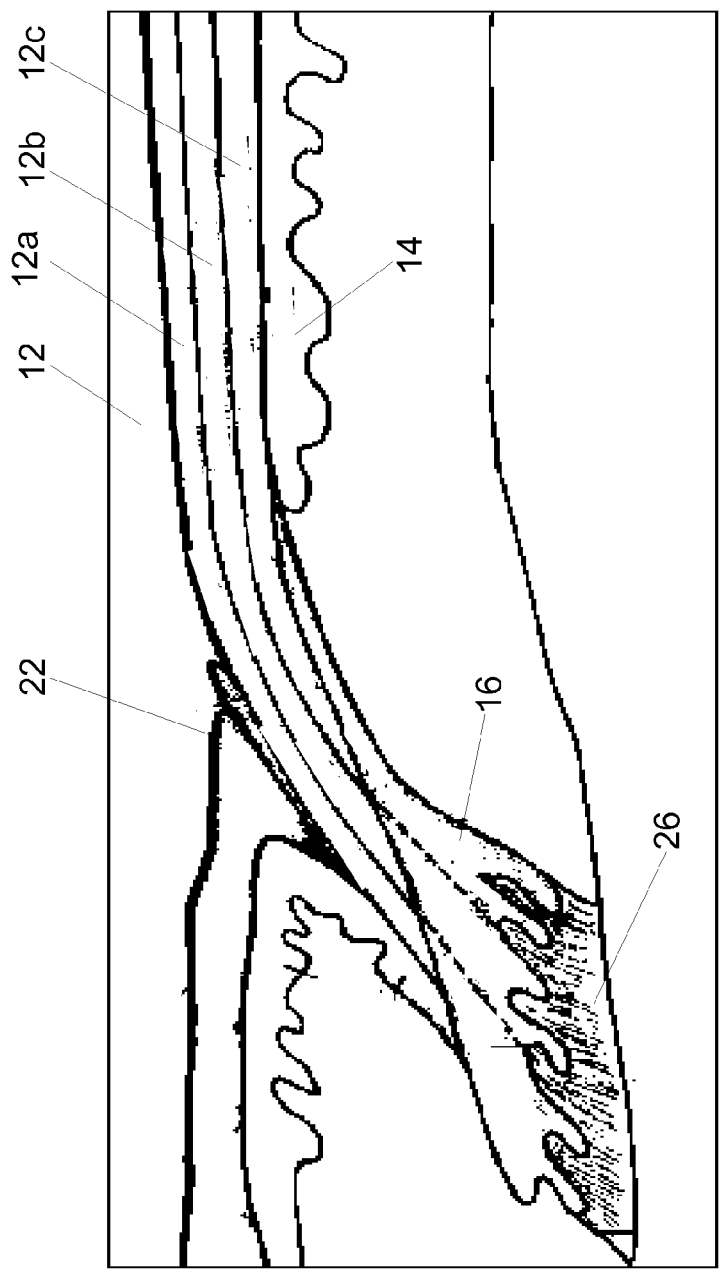
FIG. 2 shows an additional diagram of nail anatomy onto which an embodiment of the disclosed technology may be used.

FIGS. 1 and 2 show diagrams of nail anatomy onto which an embodiment of the disclosed technology may be used. The composition of the human nail is essentially a derivative of that of human skin (i.e., epidermal). The finger tip 10 is generally composed of the nail plate 12, the nail bed 14, and the nail matrix 16. The nail plate 12 is a generally thin, semi-rigid structure composed of over 20 layers of inactive keratinized flattened cells. The cells are tightly bound to one another via intercellular links, membrane-coating granules, and desmosomes. The nail plate 12 is composed generally of three layers: the dorsal layer 12a, the intermediate layer 12b, and the ventral layer 12c. Each layer has a different structure and properties.

The nail matrix 16 is protected by the nail plate 12 and is responsible for producing cells, growth of the nail, and storing nerves and blood vessels associated with the fingertip. The lunula 18 is a part of the nail matrix that is visible via the nail plate 12. The nail bed 14 is the skin directly beneath the nail plate 12, and has properties similar to that of skin covering the rest of the human body. The proximal nail fold 24 and the cuticle 22 form the junction between the hard nail plate 12 and the soft epidermis. The bone 20 of the finger resides beneath the nail bed 14.

Contrary to belief, the nail plate 12 is more permeable than human skin. (See K. A. WALTERS, *Permeability characteristics of the human nail plate*, International Journal of Cosmetic Science 5, 231-246, 1983). The presence of oxygen, nerves and blood vessels directly below the permeable nail plate facilitate greater absorption of fluids through human nails. As such, the nails may be an ideal membrane for effectively administering drugs into the bloodstream, without making incisions or puncturing the skin.

Forskolin, also known as Colforsin, 7-beta-acetoxy-8,13-epoxy-1-alpha, 6-beta, 9-alpha-trihydroxylabd-14-en-1'-one, and Coleonol has been demonstrated to have considerable positive results on subjects when applied orally and/or topically to skin. Forskolin is a labdane diterpenoid with antihypertensive, positive inotropic, platelet aggregation inhibitory and adenylate cyclase-activating properties. The activation of adenylate cyclase results in increased intracellular cyclic AMP in most tissue and cells. The molecular formula for forskolin is C22H34O7. The skeletal formula for forskolin is:

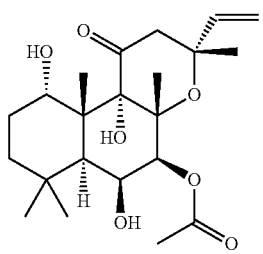

In embodiments of the disclosed technology, forskolin is incorporated into the ingredients of a nail polish or lacquer. Dissolving forskolin in a solvent enhances its permeability characteristics when applied to the human nail. For example, forskolin is soluble in organic solvents such as ethanol, chloroform, and dimethyl surfoxide. Forskolin is soluble in water (with 2% ethanol) up to 0.2 mm by first dissolving in ethanol or dimethyl surfoxide at 5 mg/mL and performing subsequent dilutions with water. Forskolin may similarly be soluble by other solvents as well.

Most nail polishes or lacquers are composed mainly of nitrocellulose dissolved in a solvent. Typically, an acetate solvent, such as, butyl acetate or ethyl acetate is used to dissolve the nitrocellulose. Other components found in nail polish and lacquers include film-forming agents, resins, plasticizers, thickening agents, other solvents, adhesive polymers, aesthetic particles, pigments and/or other coloring agents.

In forming a nail coating which employs forskolin, forskolin and nitrocellulose may be dissolved in a solvent either simultaneously, or one before the other. The solvent may be any organic solvent in which nitrocellulose and/or forskolin may be soluble. Examples of such solvents may include ethyl acetate ($C_2H_8O_2$), butyl acetate ($C_6H_{12}O_2$), dimethyl sulfoxide or "DMSO" ($C_6H_6OS$), chloroform ($CHCl_3$), ethanol ($C_2H_6O$), toluene ($C_7H_8$), water ($H_2O$), butyl alcohol ($C_4H_{10}O$), xylene ($C_8H_{10}$), and/or formaldehyde or formalin ($CH_2O$).

The composition of the nail coating may also employ any of the additional components found in nail polishes. The nail coating may be applied in various ways. The most obvious form of application is using a small brush and coating the nail with the composition, similar to the application of standard nail polish. Another way of applying the coating may involve immersing an individual's fingertips in a solution which is partially composed of forskolin, or wrapping the fingertips in solution-soaked membrane. The coating of the nail plate 12 with a forskolin-rich compound causes the nail to slowly absorb the compound into the bloodstream.

Depending on the additives used in the nail coating, the forskolin may have different rates of permeability through the nail plate 12. For example, forskolin may be absorbed using iontophoresis or by formulating the drug within a vehicle which enables high drug partition out of the vehicle and into the nail plate. Different vehicles may be included in the coating in order to facilitate greater absorption. These agents may be, for example, thiols, sulphides, hydrogen peroxide ($H_2O_2$), urea, water, and/or enzymes, each of which is known to enhance permeation. Forskolin and other compounds may be configured to be slowly released, over time, acting as a sort of time-release drug delivery system.

Permeation through the nail plate 12 may also be enhanced using physical techniques. Nail abrasion, either performed manually or electrically, reduces the thickness of the nail plate and provides at least a partial bypass of the dorsal layer of the nail plate 12, which is the hardest and least permeable layer. Acid etching, laser ablation, and microporation are other techniques which may be used to enhance absorption across the nail plate. Furthermore, low-frequency ultra-sound and electric currents may be applied to the fingertip and/or the nail plate to enhance absorption.

Figure 3:
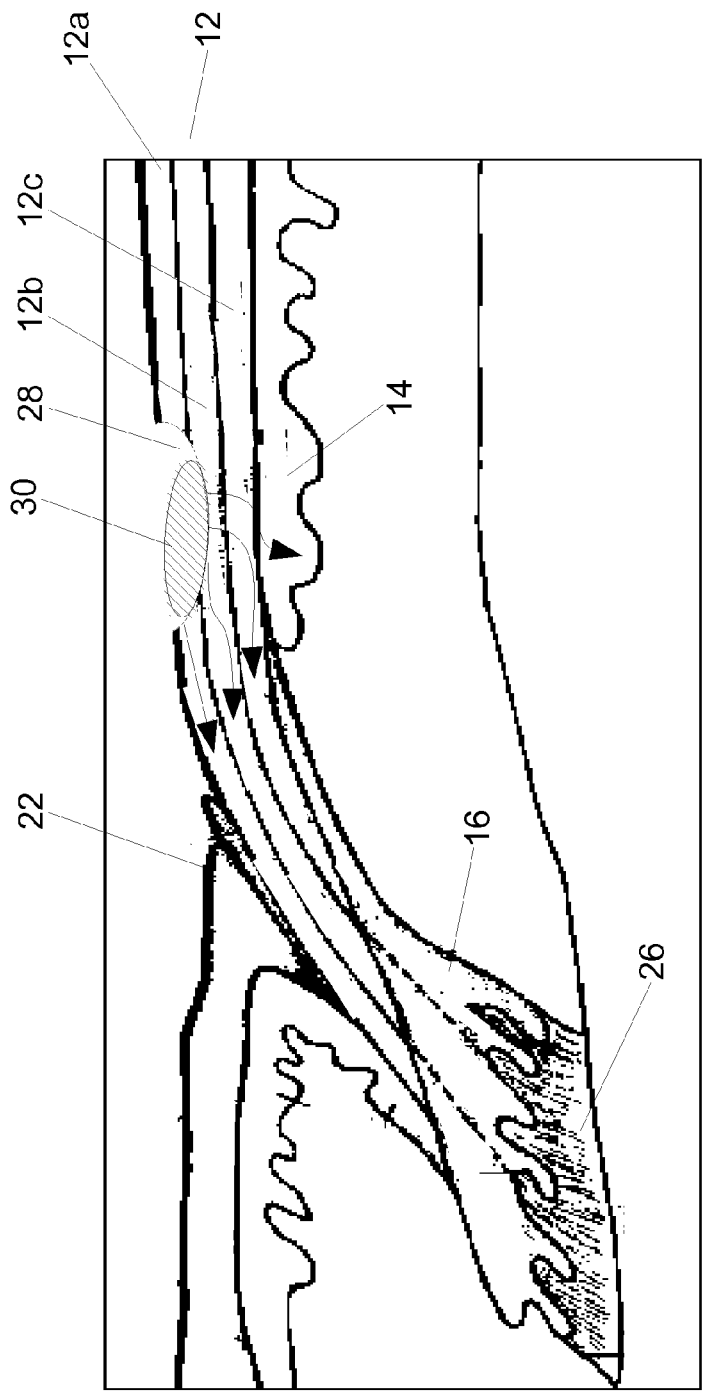
FIG. 3 shows permeation of a compound through the nail plate, according to embodiments of the disclosed technology.

FIG. 3 shows permeation of a compound through a physically modified nail plate, according to embodiments of the disclosed technology. As described, the compound 30 may be at least partially composed of forskolin. A cavity 28 is bored through the surface of the nail plate 12. The scale and size of the cavity 28 may be exaggerated in the figure for explanatory purposes. The cavity 28 is bored deep enough to facilitate access to the intermediate layer 12b of the nail plate 12. As such, the harder and less permeable dorsal layer 12a is bypassed.

A compound 30 is shown deposited into the cavity 28 of the nail plate 12. The active ingredients of the compound 30, such as forskolin, are shown permeating throughout the fingertip 10. The active ingredients may travel through the nail plate 12 towards the nail matrix 16 to be absorbed into nerves and blood vessels 26 of the finger. Further, the active ingredients are shown permeating towards the nail bed 14, whereby they may also be absorbed into the bloodstream.

As explained, different compositions with which the forskolin is used may have different rates of permeation. The rate of permeation through the nail may be represented as a permeability coefficient, P. This coefficient is indicative of the mass transfer rate through the nail plate membrane 12. It is calculated using the following equation:

eq. 1 where V is the volume of bathing medium in each half of the diffusion cell, and dc/dt is the slope of the pseudo-steady state portion of the penetration plots, A is the diffusional area and $\Delta C$ is the concentration differential of the permeant across the membrane. Reduction in diffusional area, A, results in an increased permeability coefficient and, therefore, a greater flow rate through the nail plate 12. As such, different techniques may be employed for reducing the diffusional area, A. Techniques such as acid etching, laser ablation, microporation, application of low-frequency ultra sound, and/or application of electric currents on the fingertip and/or the nail plate may be employed to reduce the diffusional area, A.

Figure 4:
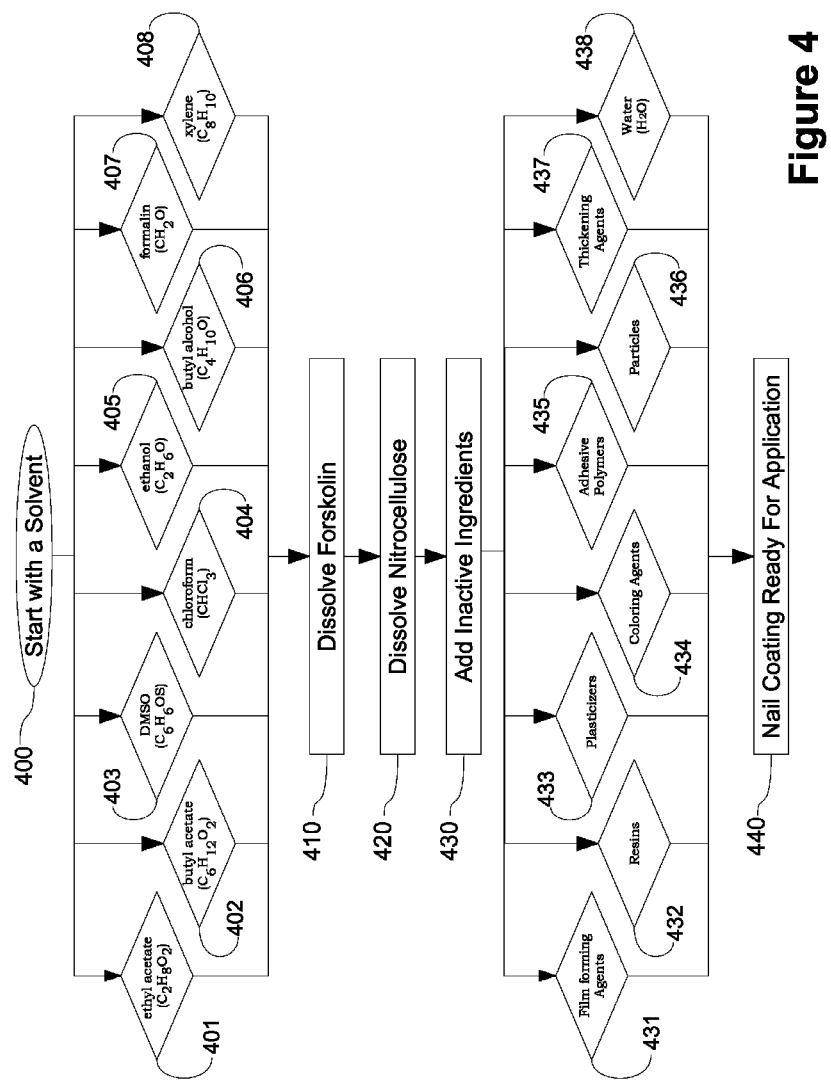
FIG. 4 shows a flow chart of steps taken in a method of preparing a nail coating, according to embodiments of the disclosed technology.

FIG. 4 shows a flow chart of steps taken in a method of preparing a nail coating, according to embodiments of the disclosed technology. The method starts with step 400, whereby a solvent is selected. The solvent may be an organic solvent as many chemicals and substances are soluble in organic solvents. Some examples of solvents chosen under step 400 include: ethyl acetate ($C_2H_8O_2$) 401, butyl acetate ($C_6H_{12}O_2$) 402, dimethyl sulfoxide or "DMSO" ($C_6H_6OS$) 403, chloroform ($CHCl_3$) 404, ethanol ($C_2H_6O$) 405, toluene ($C_7H_8$), water ($H_2O$), butyl alcohol ($C_4H_{10}O$) 406, xylene ($C_8H_{10}$) 408, and/or formaldehyde ($CH_2O$) 407. Each of these solvents is capable of dissolving forskolin and/or nitrocellulose to some degree, with varying efficacy. More than one solvent may be employed, depending on solubility, nail coating properties, and health side effects.

Forskolin, in its natural form, exists as a white/yellow cast powder. Forskolin is prepared and harvested by grinding the roots of a *Coleus Forskohlii* plant. The raw material may be purified, using a purification process after grinding. Silica chromatography is one example of a process that may be used to purify the raw material in order to yield the white/yellow cast powder.

In step 410, the forskolin is dissolved into the selected solvent(s). This step may require multiple iterations of dilutions, in order to properly dissolve the forskolin. Different solvents have different solubility compatibility with forskolin. Proceeding with the method, step 420 involves dissolving nitrocellulose or a comparable polymer into the solvent. Nitrocellulose is a thick polymer derived from cellulose treated with sulfuric and nitric acids. The nitrocellulose used in conjunction with the disclosed technology may be diluted with water or some other inactive liquid or substance. Alternatively, different polymers or polymer-like compounds may be used, as known in the art in nail polish, lacquer and coating preparation.

Referring still to FIG. 4, the method proceeds with step 430, whereby additional inactive ingredients are added to the solvent. Such inactive ingredients may be those typically added to nail polish, nail lacquer, and nail coating compositions for various purposes. Some examples of such ingredients may include, but are not limited to, film forming agents 431 (e.g., silver hallide), resins 432 (e.g., formaldehyde resin), plasticizers 433 (e.g., camphor), coloring agents 434 (e.g., pigments or dyes), color-bearing chemicals (e.g., chromium oxide greens), adhesive polymers 435 (e.g. tosylamide-formaldehyde), particles 436 (e.g. glitter or mica), thickening agents 437 (e.g. stearalkonium hectorite), UV stabilizers (e.g. benzophenone-1), magnetic particles, vitamins (e.g. vitamin D or keratin), supplements (e.g., garcinia cambogia extract), and/or water 438. Garcinia cambogia extract is another naturally occurring compound found in garcinia cambogia fruit. The chemical formula for the compound is HCA (hydroxycitric acid). The compound may block fat production and storage in humans. As such, garcinia cambogia is another compound that may be used in addition, or as an alternative, to forskolin in a nail coating composition.

In step 440, the nail coating is prepared for application and distribution. Heating and/or cooling may additionally be required to facilitate mixing of compounds and other chemical reactions. Depending on the contituents used, the nail coating may be required to be sealed, refrigerated, and/or used by a specific expiration date.

Figure 5:
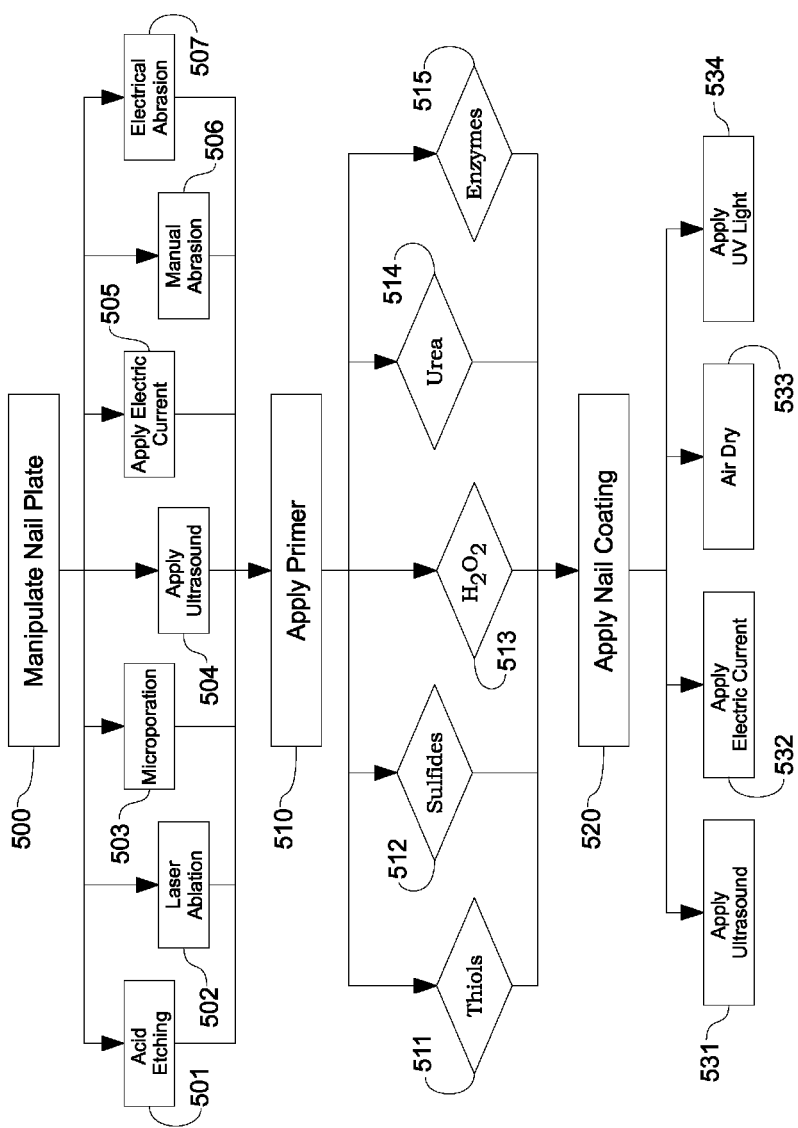
FIG. 5 shows a flow chart of steps taken in a method of applying a nail coating, according to embodiments of the disclosed technology.

FIG. 5 shows a flow chart of steps taken in a method of applying a nail coating according to embodiments of the disclosed technology. The method begins with step 500, whereby the nail plate may be altered, reduced, or otherwise manipulated to promote permeation. Some physical techniques for promoting absorption include acid etching 501, laser ablation 502, microporation 503, application of low-frequency ultrasound 504, application of an electrical current 505, manual abrasion of the nail plate surface 506, and/or electrical abrasion of the nail plate surface 507.

Proceeding with the method, step 510 is directed to applying a primer to the nail plate. The primer may be any chemical or composition that may act as a "vehicle" to forskolin absorption through the nail. The most common and obvious of these vehicles is water, in view of the fact that the nail plate is liquid permeable. Other compounds that may be used to enhance permeation include various thiols 511 and sulfides 512, hydrogen peroxide 513 ($H_2O_2$), urea 514, and/or various enzymes 515.

After a primer has been applied, the forskolin-containing nail coating is applied in step 520. The nail coating may be applied in any manner. That is, the viscous coating may be painted on with a brush, sprayed on by using compressed air, soaked in by the fingertips, and/or applied to a fabric and wrapped around the fingertips. Immediately upon application, the forskolin begins to permeate through the nail plate and/or nail matrix. After application, further steps may be taken to facilitate permeation. Again, ultrasound 531 and an electrical current 532 may be applied to the fingertips to promote permeation. The application of ultrasound 531 and an electric current 532 causes blood and oxygen to circulate throughout the fingertip, thereby promoting absorption into the bloodstream of the active ingredients of the nail coating. The freshly applied nail coating may simply be allowed to air dry 533, or a dryer may be directed onto the fingertips. In a further embodiment, ultraviolet light (UV) may be applied 534 to the fingernails. The UV light helps to dry the nail coating and may enhance permeation of forskolin through the nail plate. Additional coats may continue to be applied after the first one. Furthermore, after the intial forskolin coat has been applied, a regular nail polish may be applied to cover the initial coat.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

We claim:

1. A nail polish composition, comprising:
    a solvent;
    nitrocellulose dissolved in said solvent; and
    forskolin dissolved in said solvent.
2. The composition of claim 1, wherein said solvent is an organic solvent.
3. The composition of claim 2, wherein said organic solvent is selected from the group consisting of ethyl acetate ($C_2H_8O_2$), butyl acetate ($C_6H_{12}O_2$), dimethyl sulfoxide ($C_6H_6OS$), chloroform ($CHCl_3$), ethanol ($C_2H_6O$), toluene ($C_7H_8$), water ($H_2O$), butyl alcohol ($C_4H_{10}O$), xylene ($C_8H_{10}$), and formaldehyde ($CH_2O$).
4. The composition of claim 1, further comprising a resin.
5. The composition of claim 4, further comprising an adhesive polymer.
6. The composition of claim 5, further comprising a plasticizer.
7. The composition of claim 5, further comprising a coloring agent.
8. The composition of claim 1, further comprising urea.
9. The composition of claim 3, further comprising urea.
10. A method of preparing a forskolin nail coating, comprising:
    dissolving forskolin between 0.1 and 100 mg/ml in a solvent, said solvent comprising at least 50% ethanol; and
    dissolving nitrocellulose into said solvent until said solvent is composed between 5% and 20% of nitrocellulose.
11. The method of claim 10, wherein said solvent is composed between 10% and 15% of nitrocellulose.
12. The method of claim 10, wherein said solvent is comprised of at least 75% ethanol.
13. The method of claim 10, wherein the forskolin nail coating further comprises a plasticizer.
14. The method of claim 13, wherein the forskolin nail coating further comprises an adhesive polymer.
15. A method of ingesting forskolin comprising:
    priming a surface of a nail plate of a fingertip, wherein said priming comprises physically altering said nail plate to improve liquid permeability; and
    applying the nail polish composition of claim 1 to said nail plate.
16. The method of claim 15, further comprising a step of applying low-frequency ultrasound to said fingertip.
17. The method of claim 15, further comprising a step of applying an electical current to said fingertip.
18. The method of claim 15, wherein a concentration of said forskolin is between $10^{-4}$ mol/L and $10^{-6}$ mol/L.
19. The method of claim 15, wherein said step of priming further comprises making an abrasion on said nail plate.

* * * * *